(12) United States Patent
Begelman et al.

(10) Patent No.: US 12,290,388 B2
(45) Date of Patent: *May 6, 2025

(54) COMPUTED TOMOGRAPHY (CT) IMAGING SYSTEM, RADIATION IMAGING SYSTEM, AND METHOD OF ACQUIRING CT IMAGING DATA

(71) Applicant: CANON MEDICAL SYSTEMS CORPORATION, Tochigi (JP)

(72) Inventors: James Lawrence Begelman, Evanston, IL (US); Kevin Zimmerman, Sturtevant, WI (US); Thomas Labno, Palatine, IL (US); John Baumgart, Hoffman Estates, IL (US); Akira Nishijima, Nasushiobara (JP); Takashi Ohshima, Sakura (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 293 days.

This patent is subject to a terminal disclaimer.

(21) Appl. No.: 17/820,446

(22) Filed: Aug. 17, 2022

(65) Prior Publication Data

US 2023/0110667 A1 Apr. 13, 2023

Related U.S. Application Data

(63) Continuation-in-part of application No. 17/499,720, filed on Oct. 12, 2021, now Pat. No. 11,921,058.

(51) Int. Cl.
*A61B 6/03* (2006.01)
*A61B 6/42* (2024.01)
*G01T 1/29* (2006.01)

(52) U.S. Cl.
CPC ............ *A61B 6/032* (2013.01); *A61B 6/4241* (2013.01); *G01T 1/2985* (2013.01)

(58) Field of Classification Search
CPC ......... A61B 6/4241; A61B 6/032; A61B 6/56; A61B 6/4233; A61B 6/54; A61B 6/4266;
(Continued)

(56) References Cited

U.S. PATENT DOCUMENTS 9,964,650 B2 5/2018 Cho
10,396,109 B2 8/2019 Iniewski et al.
(Continued)

FOREIGN PATENT DOCUMENTS

GB 2600550 A 5/2022
WO 2010062465 A1 6/2010

OTHER PUBLICATIONS

Non-Final Office Action for U.S. Appl. No. 17/499,720, dated Jun. 20, 2023.

*Primary Examiner* — Irakli Kiknadze
(74) *Attorney, Agent, or Firm* — Canon U.S.A., Inc. IP Division

(57) ABSTRACT

A computer-tomography (CT) imaging system, comprising an imaging data acquisition system. The imaging data acquisition system includes a detector section, an aggregation section, and a storage section. The detection section includes a plurality of detector elements configured to convert radiation into electric signals. The aggregation section aggregates imaging data carried by the electric signals from the detector section. The storage section is arranged in a manner corresponding to the detector elements regarding an output from the detector section and an input to the aggregation section. The storage section includes a predetermined number of non-volatile memories configured to store the imaging data from the corresponding detector elements.

20 Claims, 7 Drawing Sheets

(58) Field of Classification Search
CPC ....... A61B 6/4411; A61B 6/502; A61B 6/504; A61B 6/42; A61B 6/037; A61B 6/465; A61B 5/7475; A61B 6/548; A61B 6/03; A61B 6/4494; G01T 1/2985; G01T 1/17; G01T 1/245; G01T 1/244; G01T 7/00; G01T 1/247; G01T 1/242; G01T 1/1606; G01T 1/026; G01T 1/243; G01T 1/249; G01T 1/366; G01T 1/2018; G01N 23/046; G01N 2223/3303; G01N 2223/501; G01N 2223/304; G01N 2223/50; G06T 7/0012; G06T 2207/10081; G06T 2207/10116; H04N 5/32; H04N 23/30; H04N 5/367; H04N 5/37455; H04N 5/378; G21K 2207/00; H05G 1/00; G06F 13/4022; G06F 13/4045; G06F 9/30007; G06F 9/3867; H10B 80/00; H10B 43/27; H10B 43/40; G11C 16/0483; H01L 25/0657; G21F 1/085; H03M 1/123; G16H 30/20; G16H 50/20
USPC .................................................. 378/4, 19, 62
See application file for complete search history.

(56) References Cited

U.S. PATENT DOCUMENTS

| | | |
|---|---|---|
| 10,743,826 B2 | 8/2020 | Cao et al. |
| 11,921,058 B2 * | 3/2024 | Begelman ................ A61B 6/56 |
| 2018/0217271 A1 | 8/2018 | Cho |
| 2019/0104940 A1 | 4/2019 | Zhou et al. |
| 2022/0036605 A1 | 2/2022 | Riddell et al. |

* cited by examiner

COMPUTED TOMOGRAPHY (CT) IMAGING SYSTEM, RADIATION IMAGING SYSTEM, AND METHOD OF ACQUIRING CT IMAGING DATA

CROSS-REFERENCE TO RELATED APPLICATIONS

This application is a continuation-in-part of U.S. application Ser. No. 17/499,720, which was filed on Oct. 12, 2021.

BACKGROUND

Field of Art

The present disclosure relates to a computer tomography (CT) scan/imaging system, and more particularly, to a data acquisition method and a data acquisition structure of a CT scan system.

Description of the Related Art

Traditionally, CT scanners use energy-integrating detectors which convert x-ray photons into a shower of visible light photons. The visible light is then incident on an underlying light sensor to generate positive and negative electrical charges. The recently developed photon counting detectors, on the other hand, do not require to convert x-ray into light, but converts the individual x-ray photons directly into an electric signal. The CT imaging system using the photon counting detectors provides higher contrast-to-noise ratio, improved spatial resolution, and optimized spectral imaging. Photon counting CT imaging system also reduces radiation exposure, reconstruct images at a higher resolution, corrects beam-hardening artifacts, optimizes the use of contrast agents, and creates opportunities for quantitative imaging relative to the traditional CT technology.

Photon counting CT imaging systems typically generates data with a rate around 80 GB/sec with many additional measurements that are made for each image pixel. In a CT imaging system, data acquisition hardware is constructed to continuously rotate around a patient. A mechanical/electric connection called a slip ring has been used to send data from the rotating portion to a console. The slip ring is an expensive component that may send data up to 4 GB/sec. While the slip ring can be reconfigured to send data at a higher rate, it is cost prohibitive to do so. To handle the high data rates, electronics for aggregating the measurements downstream to the detectors has been developed. The measurements are buffered on the rotating part of the CT gantry assembly. The buffer can be read in a variety of ways to support various cases such as streaming the data to a console in real time or read the data in a non-real-time manner after acquisition for post procedure processing.

However, as the detector field of view, that is, the number of detectors used in the photon counting CT imaging system, increases, the data rate can even reach 320 GB/sec. This becomes very challenging for the current electronic and storage design.

SUMMARY

A computer-tomography (CT) imaging system comprising an imaging data acquisition system is provided. The imaging data acquisition system comprises a detector section, a storage section, and an aggregation section. The detector section includes a plurality of detector elements configured to convert radiation into electric signals. The aggregation section aggregates imaging data carried by the electric signals from the detector section. The storage section is arranged in a manner corresponding to the detector elements regarding an output from the detector section and an input to the aggregation section. The storage section comprises a predetermined number of non-volatile memories to store the imaging data from the corresponding detector elements.

Each of the detector elements may include a predetermined number of detector crystals converting X-ray photons into the electric signals. A plurality of ASICs may be used to sample the electric signals from the detector elements. The storage section may include a field programmable gate arrays (FPGA) connected to the detector elements via the ASICs. The FPGAs is connected with a predetermined number of the non-volatile memories and controls the detector elements as PCIe devices. The storage section may control the detector section and the memories as NVME-interface devices. The storage section may further be programmed in parallel by multicasting PCIe commands to trigger the detector elements to collect simultaneously. The non-volatile memories may be commercial off the shelf memories and are removable from the imaging acquisition system. The aggregation section comprises a plurality of PCIe switches arranged in a tree topology.

The storage section may be integrated within the detector section. In another embodiment, the detector section, the storage section, and the aggregation section are in the form of three separate modules. Or alternatively, the storage sections may also be integrated within the aggregation sections.

The CT imaging system further comprises a slip ring connecting a rotating portion and a stationary portion of the CT imaging system. The detector sections, the storage sections, and the aggregation sections are arranged in the rotating portion. A pair of PCIe buses may be arranged across the slip ring. The CT imaging system further comprises a process computer to process data transmitted from the aggregation sections via the slip ring. The data process computer may comprise a file system configured to directly access any one set of the detector sections, the storage sections, and the aggregation sections. In one embodiment, the file system is configured to simultaneously access a predetermined number sets of the detector sections, the storage sections, and the aggregation sections.

A radiation imaging system comprising a rotating portion and a non-rotating portion is provided. There are mounted on the rotating portion: a radiation source configured to generate radiation to be incident on an object, a detector device configured to detect radiation having being transmitted through the object, a storage device configured to store imaging data generated from the detector device; and an aggregator configured to aggregate the imaging data stored in the storage device. The non-rotating portion comprises a process computer to process the imaging data having being transmitted from the rotating portion. The radiation imaging system further comprises a slip ring configured to transmit the imaging data between the rotating portion and the non-rotating portion. The storage device includes a plurality of removable non-volatile memories arranged in a manner corresponding to the plurality of detector elements in the detector device regarding an output from the detector device and an input to the aggregator. In addition, the detector device may include a plurality of detector elements, and each detector element is connected with at least one corresponding non-volatile memory, such that the imaging data of each of the detector element can be stored individually.

The radiation imaging system uses a single photon counting or a non-photon counting detector module has the capability to store the data generated by multiple scans with the commercial off the shelf removable storage technology. The aggregator is able to present at least one storage and detector module as a single data source or device in the system. The aggregator may be present anywhere between the detector and the slip ring communication link. The slip ring is configured to relay packets from one PCIe bus to another PCIe bus across the slip right. The radiation imaging system further comprises a file system logically mounted on the module of the detector device, the storage device, and the aggregator to allow standard file input/output (I/O) to and from the detector device as a single volume. The file system further allows individual module of the detector device, the storage device, and the aggregator to be accessed using standard file I/O.

A method of acquiring computer-tomography (CT) imaging data is provided. CT imaging data of an object are generated by a plurality of detector elements at a rotating side of a CT imaging apparatus. At least one non-volatile memory is provided to each of the detector elements at the rotating side. The CT imaging data from each of the detector elements are stored into the non-volatile memory corresponding to the detector element. The CT imaging data stored in the non-volatile memory of each of the detector element are combined into aggregated imaging data at the rotating side. The aggregated CT imaging data are then transmitted across a slip ring of the CT imaging apparatus to a stationary side of the CT imaging apparatus.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

So that features and advantages can be understood in details, a more particular description of embodiments of the invention may be had by reference to the embodiments illustrate in the appended drawings. It is to be noted, however, that the appended drawings only illustrate typical embodiments of the invention and are therefore not to be considered limiting of its scope, for the invention may admit to other equally effective embodiments.

DETAILED DESCRIPTION

The present disclosure is described in further detail below with reference to accompanying drawings and specific embodiments.

Figure 1:
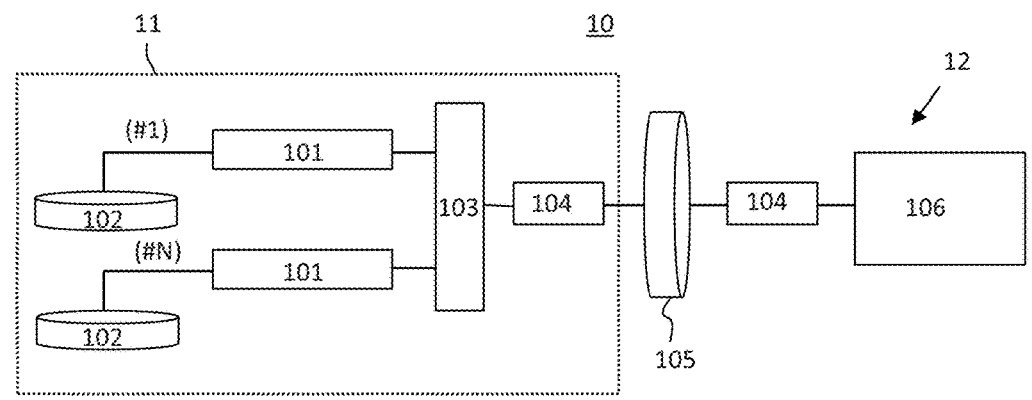
FIG. 1 is a schematic diagram of an imaging data acquisition structure according to one embodiment of the current disclosure.

The CT imaging system (computed tomography imaging system) typically includes a gantry, which may include a rotating portion framed with an X-ray source and a detector array, and a stationary (non-rotating) portion. As shown in FIG. 1, a CT imaging system includes a slip ring 105 connecting a rotating portion 11 and a stationary portion 12 of the CT imaging system. The X-ray emits X-ray beams incident on an object to be inspected. The X-ray beams traveling through the object are attenuated thereby and then received by the detector array. The detector array converts the photons of the attenuated X-ray beams into electric signals to be processed and analyzed for diagnose. The imaging data carried by the electric signals may be acquired and processed by an imaging data acquisition structure as shown in FIG. 1. As shown, the imaging data acquisition structure 10 includes a portion located in the rotating portion 11 of a gantry and another portion in the non-rotating portion (stationary portion) 12. An array of detectors 101 (#1) to (#N) are located in the rotating portion 11 to detect the X-ray beams from the object. Each of the detector elements 101 (#1) to (#N) is connected with a corresponding memory 102 ((#1) to (#N)). To eliminate high data rates, non-volatile memories are used in the current embodiment. As each detector element, that is, imaging detector 101, contributes a small fraction of the aggregate data rate, the storage can be designed to accommodate the lower data rate from an individual detector 101; or alternatively, a small group of detectors (see FIG. 2). The memories 102 may be selected from commercial off the shelf storage components. For example, non-volatile storage technology used in the current embodiment may be flash-based, CFExpress, SDEpress, or XFMExpress form factors and NVME access protocols. These form factors are very small with high G-load tolerance while used in a rotating environment. Each of the non-volatile storage capacity for each imaging detector may store multiple scans, for example, the scans performed in a day with the current storage technology. The bandwidth of each of the memories 102 is about 1 to 2 GB/sec, for example. The data imaging data acquisition structure 10 further includes an aggregation and control device 103 to aggregate the imaging data from the array of detectors 101. The aggregation and control device 103 may be configured to handle a data rate at 80 GB/sec, for example. The imaging data aggregated by the aggregation and control device 103 is transmitted via the slip ring 105 with a bandwidth about 4 GB/sec. The imaging data is then transmitted from the slip ring 105 to a data process and display computer 106. That is, the slip ring 105 transmits the imaging data between the rotating portion 11 and the non-rotating portion. In this situation, the data process and display computer 106 includes a process computer to process data transmitted from a later-described aggregation section via the slip ring 105. In the embodiment as shown in FIG. 1, a bridge 104 is used across the slip ring 105.

Figure 2:
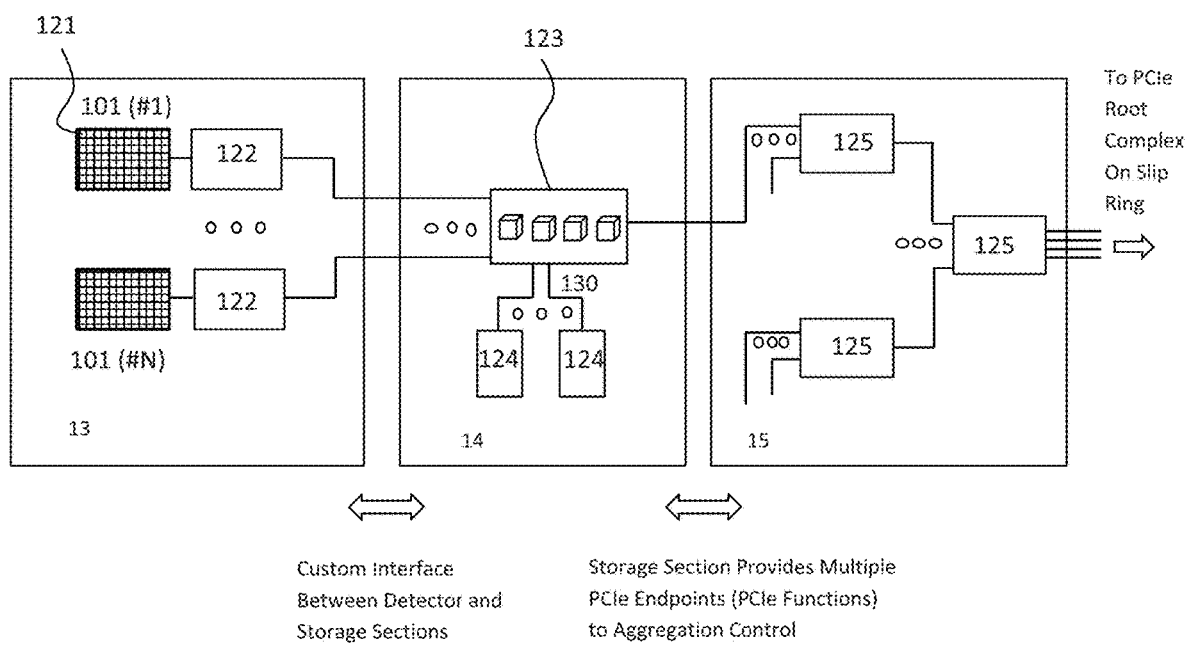
FIG. 2 is a block diagram of logic architecture of an imaging data acquisition structure according to one embodiment of the current disclosure.

FIG. 2 is a block diagram of logic architecture of an imaging data acquisition structure used in the photon counting CT imaging system according to one embodiment. In FIG. 2, each block may represent a semiconductor chip or circuitry which provides the desired functionalities, while each cube may represent a firmware. The imaging data acquisition structure in the rotating portion 11 may be divided into three sections, including a detector section (detector device) 13, a storage section (storage device) 14, and an aggregation section (aggregator) 15. That is, the detector section 13, the storage section 14, and the aggregation section 15 are arranged in (mounted on) the rotating portion 11; and the imaging data acquisition structure includes the detector section 13, the storage section 14, and the aggregation section 15. Note that the rotating portion 11 may further have a radiation source mounted thereon, the radiation source configured to generate radiation to be incident on an object. In this situation, the imaging data acquisition structure may further include the radiation source. The detector section 13 includes a plurality of detector elements (which may be referred to as imaging detectors) 101 configured to convert radiation (for example, an X ray) into electric signals. The plurality of detector elements 101 are arranged, for example, in a rotation direction of the rotating portion 11 over a range irradiated by the radiation. Each imaging detector 101 may be formed by a number or an array of detector crystals 121. For example, each of the detector elements 101 includes a predetermined number of detector crystals converting X-ray photons into electric signals. The detector crystals 121 convert X-ray photons into electric signals. The detector crystals 121 are, for example, semiconductor detector elements that convert X-ray photons directly into electric signals. The electric signals from each imaging detector 101 are sampled by an ASIC (application specific integrated circuit) 122 connected thereto. That is, the detector section 13 includes a plurality of ASICs 122. As shown in FIG. 2, the ASICs 122 sample electric signals from their corresponding detector elements 101. The ASICs 122 may be configured to perform any selected imaging corrections and/or calibrations to the samples. As shown in FIG. 2, the circuitry uses PCIe (peripheral component interface express) or other communication standards to move the samples off the ASIC 122. The imaging data from a small number of ASICs 122 are aggregated into the storage section 14 implemented with an FPGA (field programmable gate array) 123 attached with arrays of storage devices or non-volatile memories 124. That is, the storage section 14 includes the FPGA 123 connected to the detector elements 101. As shown in FIG. 2, the FPGA 123 is connected to a predetermined number of the non-volatile memories 124. The FPGA 123 may include firmware and software that represent the storage section 14 and detector section 13 as PCIe device functions. This allows the entire detector section 13 to be controlled as an array of PCIe (peripheral component interconnect express) devices which store and read acquired detector data from the detectors 101 and control the ASICs 122. Therefore, in the example as shown in FIG. 2, the interface between the FPGA 123 and the storage devices 124 includes PCIe interface 130. In other words, the FPGA 123 controls the detector elements 101 as PCIe devices.

Figure 3:
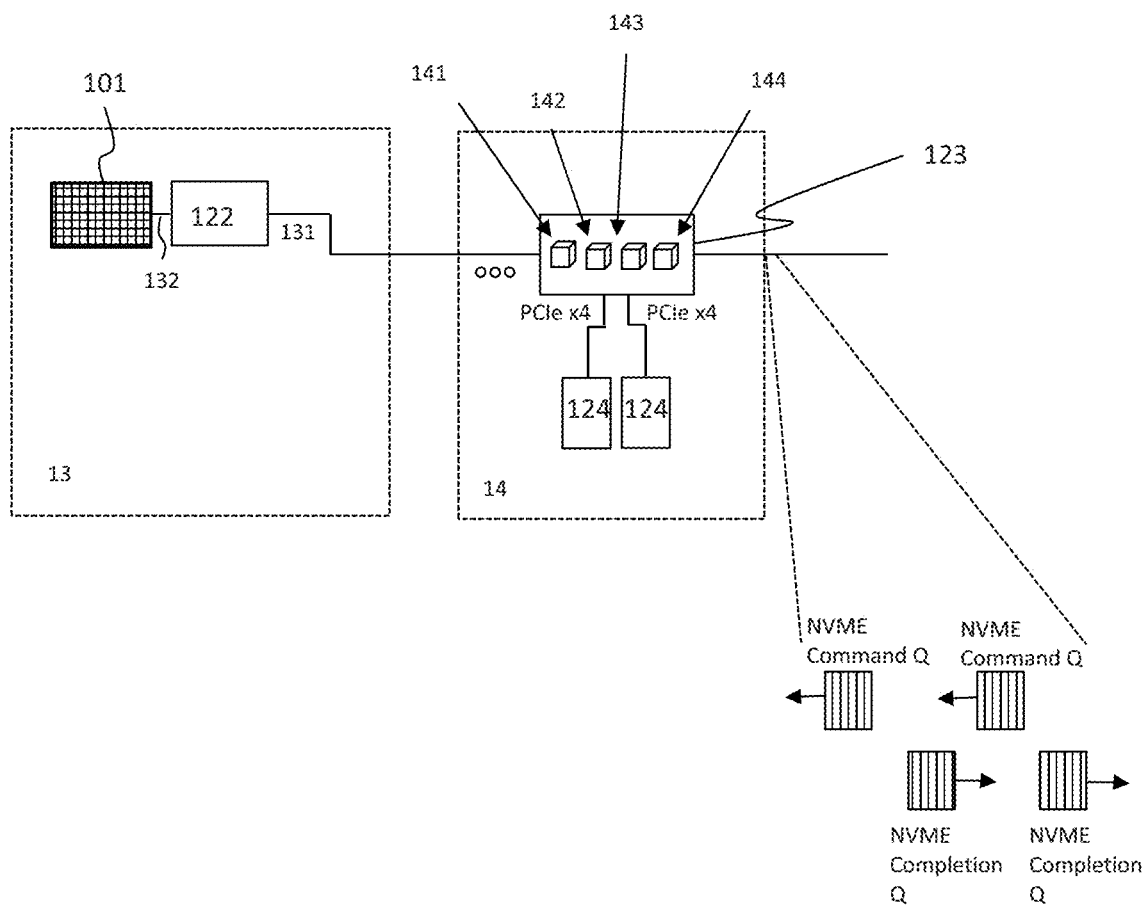
FIG. 3 is a block diagram showing the operation between the detector section and the storage section of an imaging data acquisition structure according to one embodiment of the current disclosure.

FIG. 3 shows the interface between the detector section 13 and the storage section 14 and the operation of the storage section 14. In the example as shown, bump bonds 132 are used to connect the detectors (detector elements) 101 and the corresponding ASIC 122, and ASIC input/output 131 is between the ASIC 122 and the FPGA 123. In addition to the bump bonds, other types of connections such as wire bonds can also be used between the detectors 101 and the ASIC 122. As discussed above, the FPGA 123 may be implemented with firmware and software to represent the detector section and the storage section as PCIe devices. The FPGA 123 may include various blocks, that is, reusable cells or units of logic, or integrated circuit (IC) layout designs arranged for specific purpose. For example, in FIG. 3, the FPGA 123 includes an ASIC interface block 141 to interface with the ASIC 122, a NVME input/output block 142 for input/output of NVME, a compression block 143 for data compression and/or decompression, and a PCIe interface block 144 for PCIe interface. The FPGA 123 may use hard, soft, or firm Intellectual Property (IP) cores to implement the various blocks. In the current embodiment, the PCIe interface between the FPGA 123 and the array of memories 124 include 4 communication lanes (PCIex4).

To perform IO, an application sends read/write commands to the NVME storage device. The commands specify the type of IO, source, and destination address, for example. As shown in FIG. 3, the NVME storage device receives an IO command from an area, namely, a Command queue (Q), in the memory of a computer. Upon finish executing the IO command, a notification is placed in a Completion Q located in the NVME storage device. The NVME standard allows a device to have multiple command/completion Q pairs, one completion Q for every Command Q, so as to serve multiple commands in parallel from potentially multiple source.

The storage section 14 is arranged in a manner corresponding to the plurality of detector elements 101 regarding an output from the detector section 13 and an input to the aggregation section 15. For example, the storage section 14 includes a predetermined number of non-volatile memories 124 configured to store imaging data from the corresponding detector elements 101. More particularly, each of the detector elements 101 is electrically connected with at least one corresponding non-volatile memory 124. Note that the non-volatile memories may be arranged in association with the detector crystals 121. Moreover, the storage section 14 may further include a volatile memory upstream of the non-volatile memories 124. Even when the transmission rate of the non-volatile memories 124 decreases due to influence of heat, rotation of the rotating portion 11, installation space for the non-volatile memories 124, etc., because the storage section 14 includes the volatile memory, the imaging data can be written to the non-volatile memories 124 with no problem. For example, the FPGA 123 determines to decrease the writing speed to the non-volatile memories 124 on the basis of a rotating rate of the rotating portion 11 in the imaging protocol executed on the subject, and the FPGA 123 writes the imaging data to the non-volatile memories in accordance with the amount of decrease in the writing speed. Furthermore, the storage section 14 uses commercial removable storage interfaced with the NVME protocol because of the ubiquity of the NVME in the market and performance. For example, the non-volatile memories 124 are removable from the imaging data acquisition structure. The storage section 14 also controls the detector elements 101 and the storage section 14 as a NVME (non-volatile memory express)-interface devices. In this manner, the FPGA 123 presents both the ASICs 122 and the storage devices 124 as NVME devices with several unique namespaces. For example, ASIC namespaces contain a single logical block that contains the status and control bits of the ASICs 122 within well-known bit fields. Using The NVME IO, writing the block sets control bits and reading the block returns the current state of the ASIC. ASIC control fields can be defined to specify IO targets within the storage namespace so that an ASIC command initiates collection to storage. Storage namespaces contain all addressable storage blocks on the storage devices. Corresponding to data collection and readout, the storage can be written by ASIC but read by "upstream" components concurrently. More description of the namespaces will be provided with reference to FIG. 7.

Figure 4:
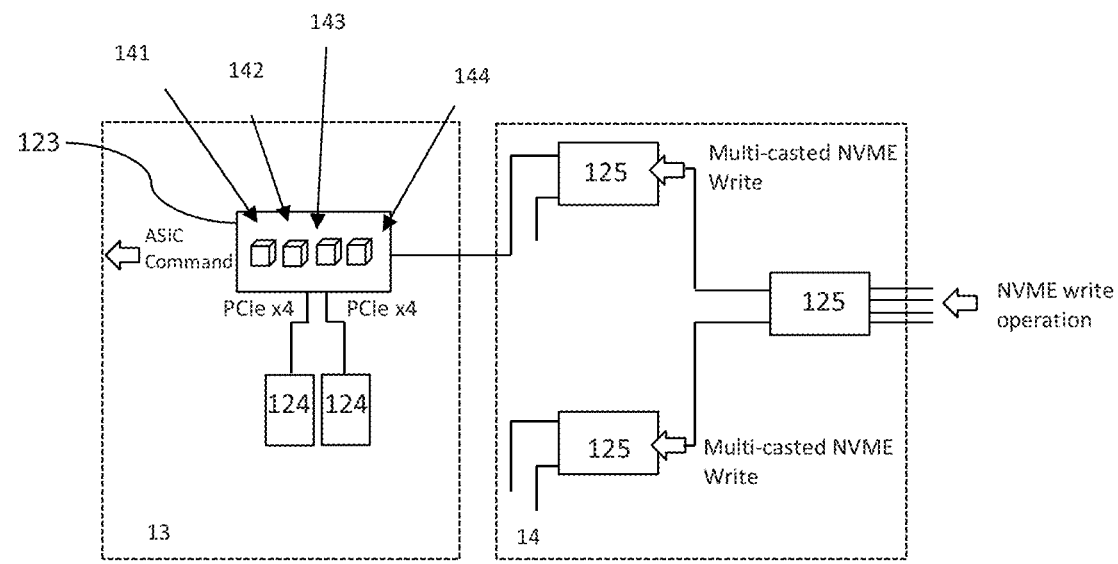
FIG. 4 is a block diagram showing the operation between the storage section and the aggregation section of an imaging data acquisition structure according to one embodiment of the current disclosure.
Figure 5A:
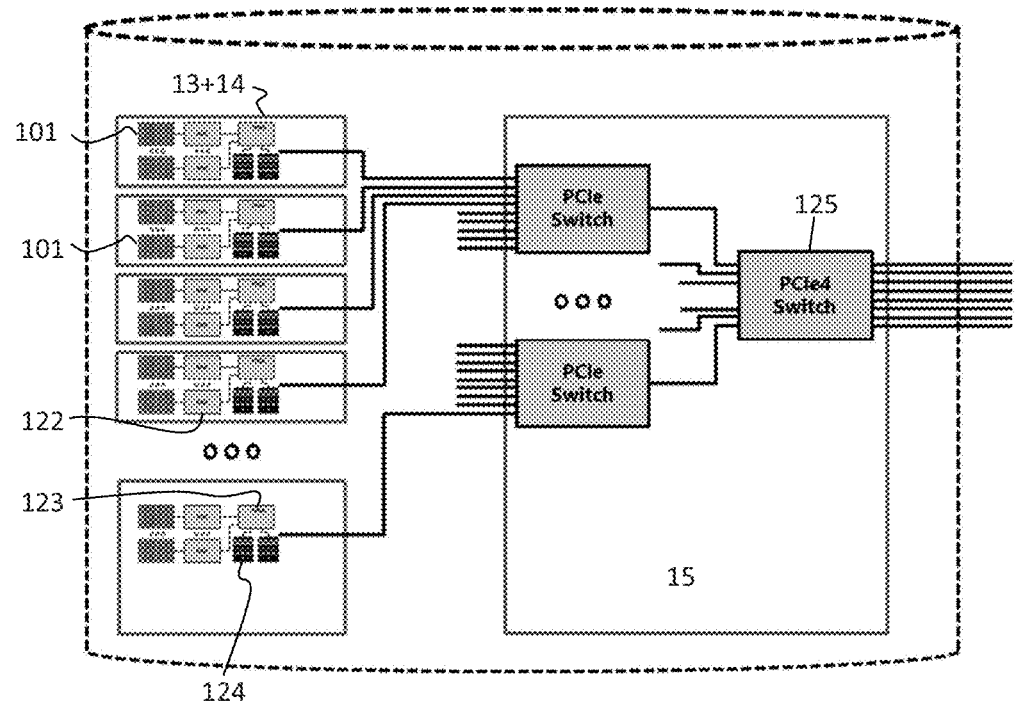
FIGS. 5A to 5C are schematic diagrams showing various layouts of the storage devices in the imaging data acquisition apparatus according to one embodiment of the current disclosure.
Figure 5B:
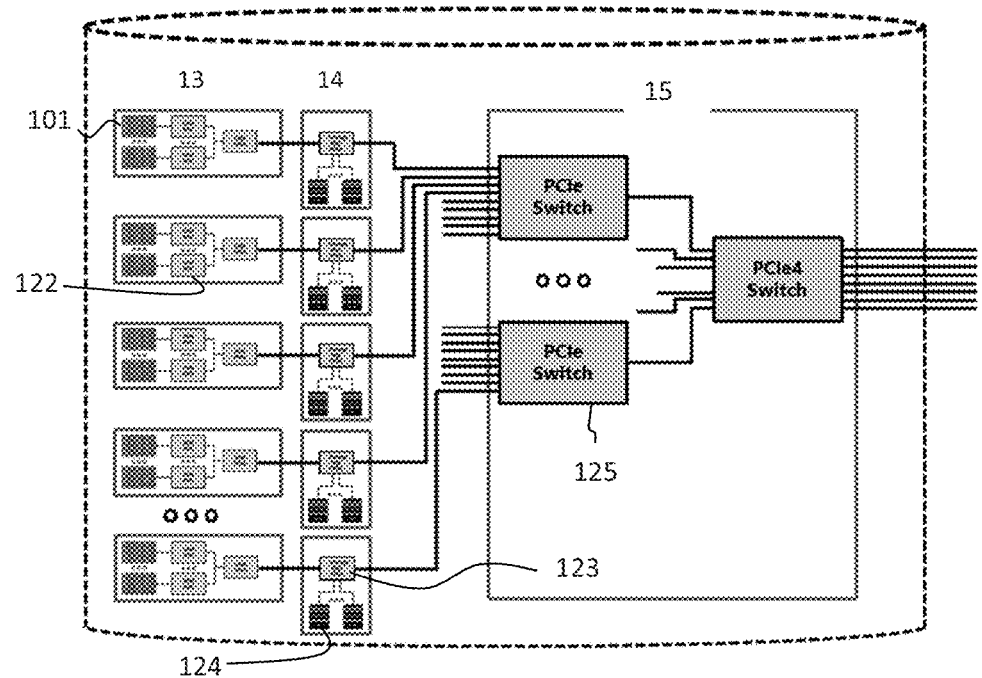

The aggregation section 15 combines data transfers from each storage section 14 corresponding to a predetermined number of detector crystals 121 and routes it to the remainder of the system. For example, the aggregation section 15 aggregates imaging data carried by the electric signals from the detector section 13. In the embodiment as shown in FIG. 2, the storage section 14 provides multiple PCIe endpoints (PCIe functions) to the aggregation section 15. The aggregation section 15 is implemented with commercial PCIe switches 125 arranged in a tree topology. That is, the aggregation section 15 includes a plurality of PCIe switches arranged in a tree topology. The number and size of PCIe switches 125 is chosen to minimize cost, yet support slip ring throughput. FIG. 4 shows the operation between the storage section 14 and the aggregation section 15 according to one embodiment of the current disclosure. In this embodiment, all storage devices can be programmed in parallel by multicasting NVME IO commands using multicast features of the PCIe protocol. For example, the storage section 14 is programmed in parallel by multicasting PCIe IO (input/output) commands to trigger the detector elements 101 to collect simultaneously. This allows the detector section 13 to be triggered to collect data simultaneously without use of special hardware lines, that is, this allows in-band signaling. As shown in FIGS. 5A and 5B, the image data acquisition structure may include multiple detector sections and multiple storage sections, and each of the detector sections may further comprise one or more detector elements 101. These detector sections may also be controlled individually. The FPGA 123 and aggregation network are so designed that an NVME device interface resides within a PCIe multicast address window. The NVME IO operations to this device are in fact multicast to each individually storage section using the PCIe protocol.

The number of the storage devices 14 in the storage section is selected to support required throughput. For example, two memories 124 are used in the storage section 14 as shown in FIG. 2. The capacity of each storage device may be scaled by purchasing the appropriate part. Current technology ranges up to 1 TB per part where only 64 GB per device might be required for a single scan. This means that a single memory used in all detector modules allow the entire system to store about 16 scans before the parts have to be read out in order to perform another scan (in practice, storage is read out continuously during and after acquisition to prevent the part from being filled).

Figure 5C:
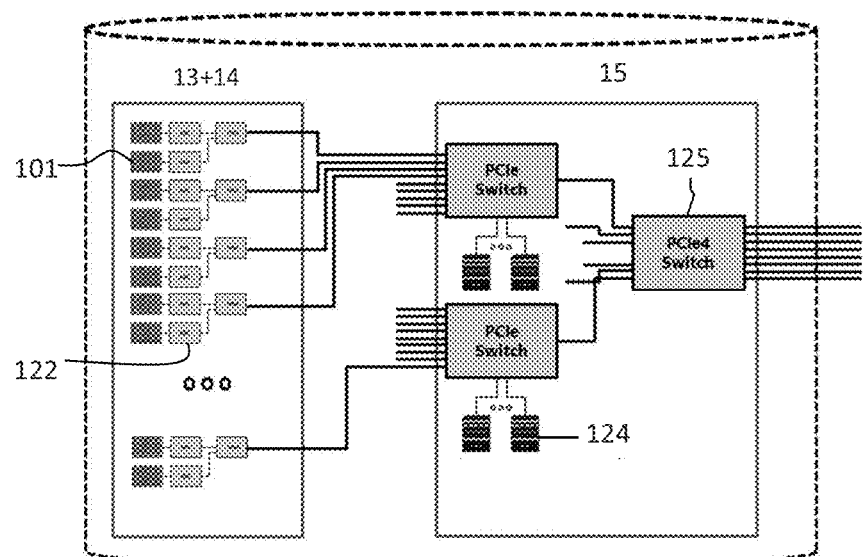

FIGS. 5A to 5C are diagrams of various embodiments in which the storage units are integrated to different positions of the imaging data acquisition structure. For example, in FIG. 5A, the storage capability, that is, at least one of multiple storage sections 14, is integrated within the corresponding detector section 13. The memories are integrated into each detector section, while multiple detector sections are connected to a common PCIe switch 125. This optimizes throughput from the detector elements. However, this might be relatively difficult to implement due to power and thermal restrictions within the detector section. In the embodiment as shown in FIG. 5B, the storage capability is integrated in its own detector section, which is physically independent of either the detector or the aggregation electronics, but stores the imaging data prior to aggregation. The separate section allows larger and wider variety of storage devices to be used in the system. That is, in the embodiment as shown in FIG. 5B, the detector section 13, the storage section 14, and the aggregation section 15 are in the form of three separate modules. However, the larger devices may mean less High-G tolerance. In FIG. 5C, the storage capability is in the front end of the aggregation electronic, that is, the end facing the detector to allow storage of imaging data prior to aggregation. Depending on ASIC-to-FPGA fan-in within the detector modules and the aggregation network that is used, this may require storage to support higher throughput. NVME storage may be directly connected to the PCIe switches 125 to simplify the design. Similar to the embodiment as shown in FIG. 5B, this may allow larger and wider variety of storage devices, which on the other hand, has less High-G tolerance. In FIG. 5C, the storage section 14 is integrated within the aggregation section 15.

In any of the layouts as shown in FIGS. 5A to 5C, the storage section 14 is arranged to store the imaging data from the detector section 13 prior to the aggregation process performed in the aggregation section 15. That is, the imaging data are output from the storage section 14 into the aggregation section 15.

In a modification of the embodiments in connection with FIGS. 5A to 5C, the storage section 14 may be arranged between the detector section 13 and the aggregation section 15 and further arranged within the detector section 13. In this situation, the present modification corresponds to a combination of the structure shown in FIG. 5A and the structure shown in FIG. 5B. In another modification, the storage section 14 may be arranged within the detector section 13 and further arranged within the aggregation section 15. In this situation, the present modification corresponds to a combination of the structure shown in FIG. 5A and the structure shown in FIG. 5C, and the storage section 14 arranged within the aggregation section 15 stores data that is obtained, for example, by executing lossy compression on the imaging data. In a further modification, the storage section 14 may be arranged between the detector section 13 and the aggregation section 15 and further arranged within the aggregation section 15. In this situation, the present modification corresponds to a combination of the structure shown in FIG. 5B and the structure shown in FIG. 5C, and the storage section 14 arranged within the aggregation section 15 stores data that is obtained by, for example, executing lossy compression on the imaging data.

In another modification of the present embodiment, a capacity of some of the non-volatile memories 124 electrically connected with some of the detector elements 101 positioned at both ends in a rotation direction of the rotating portion 11 may be smaller than a capacity of one of the non-volatile memories 124 electrically connected with one of the detector elements 101 positioned in a center portion in the rotation direction. That is, in a detection surface formed by the plurality of detector elements 101 for detecting radiation, a memory capacity (hereinafter, end-memory capacity) of a non-volatile memory 124 that stores therein output (imaging data) from a detector element (hereinafter, end element) positioned at an end in a fan-angle direction in which the radiation emitted from the radiation source makes a fan angle is smaller than a memory capacity (hereinafter, center-memory capacity) of a non-volatile memory 124 that stores therein output (imaging data) from a detector element (hereinafter, center element) positioned at the center in the fan-angle direction. In other words, the center-memory capacity is larger than the end-memory capacity. With this configuration, in the present modification, memory capacities according to amounts of information can be applied to the non-volatile memories 124, because an amount of information of imaging data output from the end element may be smaller than an amount of information of imaging data output from the center element. Thus, the present modification can provide a CT imaging system with a lower cost.

In still another modification of the present embodiment, among the plurality of detector elements 101, the detector elements 101 positioned at the both ends in the rotation direction are electrically non-connected with any of the non-volatile memories. That is, in the present modification, none of the non-volatile memories 124 are needed for the end elements. With this configuration, the present modification can provide a CT imaging system with a further lower cost than the another modification.

Figure 6:
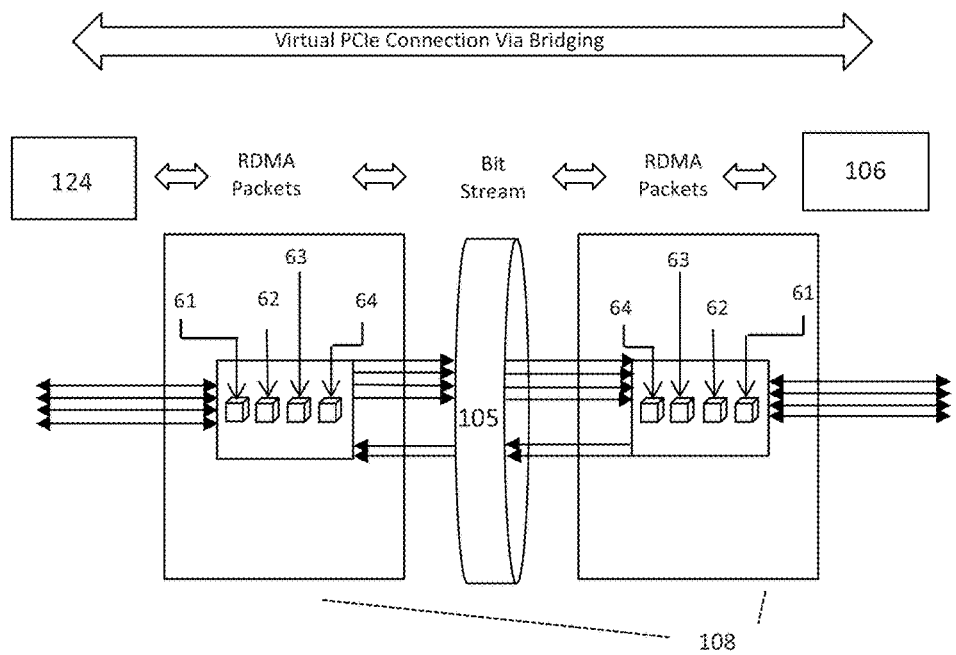
FIG. 6 is a schematic diagram of the slip ring connected between the non-rotating portion and the rotating portion of the radiation imaging system according to one embodiment of the current disclosure.

FIG. 6 is a schematic diagram showing the slip ring 105 that connects the rotating portion 11 and the stationary portion 12 of the CT imaging system. As shown, the rotating portion 11 and the stationary portion 12 of a CT imaging system are connected with a PCIe-to-PCIe bridge (104 as shown in FIG. 1) across the slip ring 105. The slip ring 105 functions as a PCIe-to-PCIe bridge to relay PCIe programmed input/output (PIO) or direct memory access (DMA) between the rotating portion and the stationary portion. This makes all components on the rotating portion 11 appear as local PCIe endpoints to the real-time computer on the stationary side. Remote direct memory access (RDMA) is a direct memory access from the memory of one computer into the memory of another computer without involving the operating system of either computer. Therefore, in the embodiment as shown in FIG. 6, RDMA packets are transmitted between the rotational side and the stationary side. The entire packets are forwarded (transmitted in bit stream) across the slip ring 105. The system and the gantry electronics are independent with each other. The devices are mirror imaged at two opposite sides of the slip ring 105. Data for transmission across the slip ring 105 may be compressed, while the received data may be decompressed. In FIG. 6, the slip ring differences, for example, allocation of upstream and downstream lanes can be hidden. In addition, the bridge between the PCIe buses can be either transparent and non-transparent. That is, the CT imaging system according to the present embodiment includes a pair of PCIe buses across the slip ring 105. In the embodiment as shown in FIG. 6, the compression and decompression are only assigned to the slip ring interface. Therefore, if a new or existing computer is used to access and manipulate the data stream, the access or manipulation can be performed directly without the need to decompress the data first. In FIG. 6, the FPGA of the PCIe bridge may include various Intellectual Property cores such as a PCIe IP 61, a RDMA IP 62, a Compression IP 63, and a Schliefring TX/RX IP 64 for PCIe interface, RDMA transmission, data compression and/or decompression, and data transmission across the slip ring, respectively.

Figure 7:
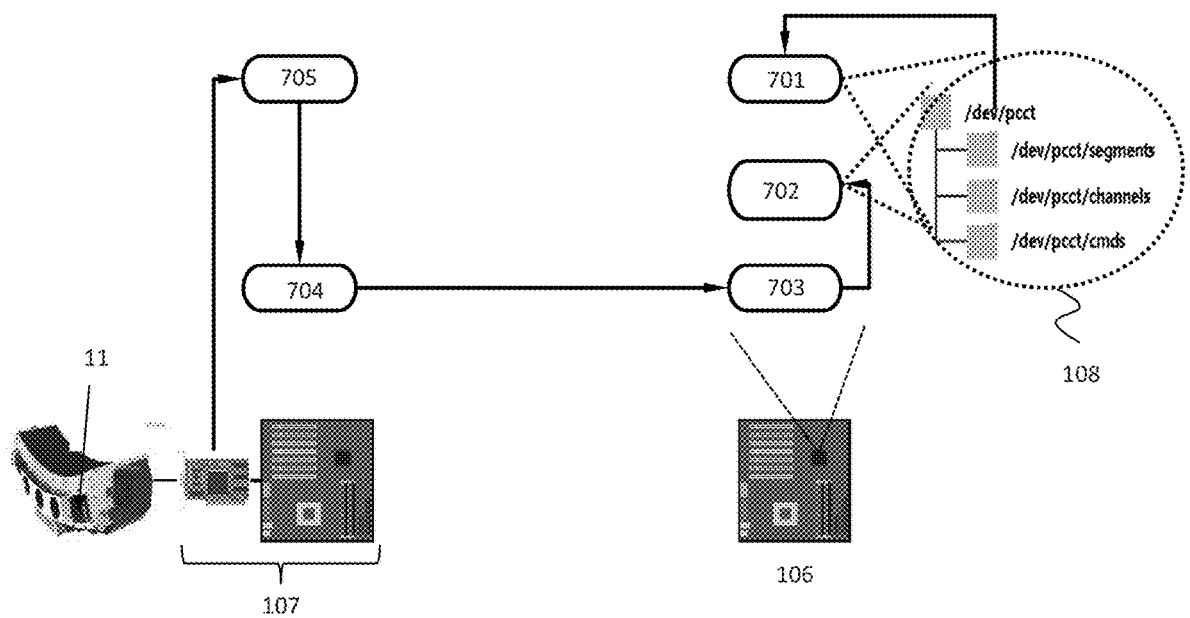
FIG. 7 is a schematic diagram of a file system flow diagram according to one embodiment of the current disclosure, in which data are transmitted from CT computer to detector.

In addition to the various physical layouts of the detector section 13 and storage section 14 as shown in FIGS. 5A to 5C, the arrangements of the detectors in the detector section 13 may also implemented by a file system. That is, the process computer in the CT imaging system includes a file system configured to directly access the detector section 13, the storage section 14, and the aggregation section 15. If, for example, the imaging data acquisition structure includes a plurality of detector sections and a plurality of storage sections, the file system may simultaneously access a predetermined number of the detector sections, a predetermined number of the storage sections, and the aggregation section 15. FIG. 7 shows an exemplary file system which uses software to model detector functions and storage. The file system may be a standard POSIX file system which provides bi-directional communication between the rotating portion 11 and the stationary portion 12 of the CT imaging system. For communication from the CT computer in the stationary portion 12 to the rotating portion 11, an application software 701 uses standard I/O operations to access a local file 108, for example, open( ), read( ), write( ), and close( ). An operating system driver (kernel module) 702 re-routes the I/O request across the slip ring 105 to a detector software 704. The detector software 704 may run on a computer 107 on the rotational side to access portion of detector storage corresponding to the I/O request. In the example as shown in FIG. 7, through libnvme (linux (registered trademark)) 705, the NVME physical I/O read/write request is issued to correct detector storage module. Libnvme is an open source library that provides type definitions for NVMe specification structures, enumerations, and bit fields, helper functions to construct, dispatch, and decode commands and payloads, and utilities to connect, scan, and manage NVMe devices on a Linux system. For the communication from the detector to the CT computer, I/O data is returned to the rotation side computer 107 from the detector. The I/O data is transmitted to the detector software 704, via which the detector data is sent across the slip ring 105 to the file system driver 703. The file system driver 703 receives I/O data and relays to application. The operating system 702 performs data copy from the file system driver 703 to the application buffer. The application software 701 receives results from I/O operations, for example, open( ), read( ), write( ), and close( ).

In FIG. 7, the file system includes a namespace, which is a directory hierarchy of the file system visible to software running on the computer 106. On a Linux system, the namespace can be used to represent various objects. For example, the file system namespace represents the arrangement of files on a disk. One can use simple file IO operations and make these IO operations mean different things depending on which portion of the namespace is accessed under Linux. For example, one can apply this to the storage detector by modifying Linux so that a certain portion of the namespace represents data stored on the detector. The namespace area used in the example as shown in FIG. 7 is named "/dev/pcct." When an application need data from the detector, the application may simply open what appears to be a file "/dev/pcct/segments" and read from it.

Figure 8:
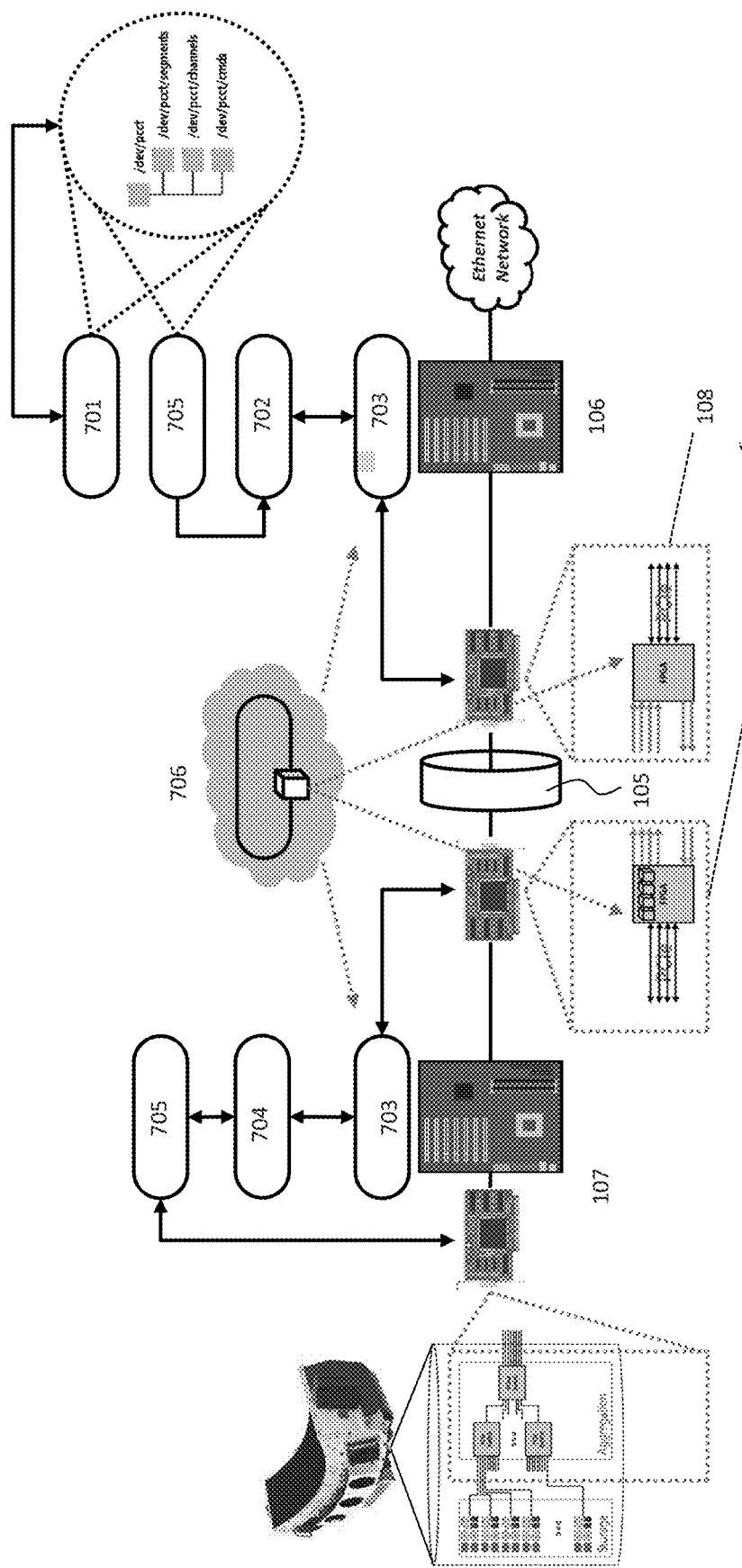
FIG. 8 is a schematic diagram of a file system flow diagram according to one embodiment of the current disclosure, in which data are transmitted from detector to CT computer.

FIG. 8 shows the CT system using the storage-detector as a file system. The software models detector functions and storage as the file system in standard UNIX (registered trademark) practice, for example. In the embodiment, libnvme 705 is used in both the rotating portion 11 and the stationary portion 12 to mount the file system to the CT system. In this embodiment, Xillybus is used as the file system driver 703 at both the rotating portion 11 and the stationary portion 12 of the CT system, the possible approach to bridge implementation with OTS tech uses Xillybus IP and software drivers 706. It is appreciated that Xillybus is only an example. The implementation can also be achieved with an FPGA and associated firmware. The file system may select the imaging data received from a selected one or group of pixels of a selected group of detector modules to be transmitted from the corresponding storage devices. In this way, detector implementation details and geometry can be hidden, and the applications can be simplified. The aggregation of data, control signals, and status may also be bypassed to permit direct addressing of an individual detector through the same file system. By selecting the imaging data received from a selected group of pixels. Any additional policies that access detector data can be modelled with the creation of new files using the same method.

Figure 9:
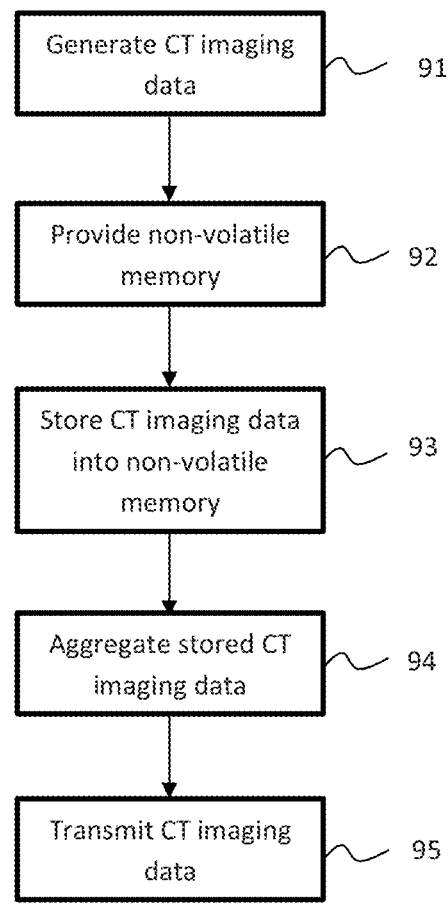
FIG. 9 is a flow chart of a method for acquiring CT imaging data according to one embodiment of the current disclosure, the method using the data acquisition structure as shown in FIGS. 1-8.

In the structures as shown in FIGS. 1 to 6, non-volatile storage may be made a part of the imaging detector itself. Since each imaging detector contributes only a small fraction of the aggregate data rate, the storage can be designed to accommodate the lower data rate from an individual detector or small groups of detectors. With such structure, CT imaging apparatus can handle a much higher data rate without increasing the load and cost of the slip ring 105. FIG. 9 shows a process flow of a CT imaging data acquisition method that uses this structure. In step S91, CT imaging data are generated by the detector section 13 at a rotating side of a CT imaging apparatus. The detector section 13 may include multiple detector elements 101. That is, the CT imaging data of the object is generated by the plurality of detector elements 101 at the rotating side of the CT imaging apparatus. Each of the detector elements is provided with at least one non-volatile memory 124 in step S92. That is, at least one of the non-volatile memories 124 is provided to each of the detector elements 101 at the rotating side. The CT imaging data of each detector element can be stored in the corresponding non-volatile memory 124 in step S93. In step S94, the CT imaging data from each of the non-volatile memories 124 are combined. That is, the CT imaging data stored in the non-volatile memory 124 of each of the detector elements 101 is combined into aggregated CT imaging data at the rotating side. The aggregated CT imaging data is transmitted across the slip ring 105 to the other side of the CT imaging apparatus, i.e., the stationary side of the CT imaging apparatus.

In an application example of the present embodiment, the aggregation section 15 may include a further non-volatile memory different from the non-volatile memories 124 in the storage section 14. Note that when the storage section 14 is provided between the detector section 13 and the aggregation section 15, the further non-volatile memory may be mounted on the storage section 14. Moreover, when the storage section 14 is provided between the detector section 13 and the aggregation section 15, function implemented with the further non-volatile memory may be implemented with the non-volatile memories 124 in the storage section 14.

The CT imaging system according to the present application example includes the rotating portion 11. The detector section 13, the storage section 14, and the aggregation section 15 are mounted on the rotating portion 11. The rotating portion 11 is rotatable around the rotation axis. The plurality of detector elements 101 are arranged in the rotation direction of the rotating portion 11. The plurality of detector elements 101 form a detection surface for detecting radiation. The detection surface has a long axis and a short axis in which, for example, the long axis extends in the rotation direction, i.e., a fan-angle direction (also referred to as channel direction) in which radiation emitted from the radiation source makes a fan angle, and the short axis extends in the rotation-axis direction, i.e., in the column direction.

Moreover, the storage section 14 according to the present application example further includes a volatile memory upstream of the non-volatile memories 124. The above-mentioned non-volatile memories 124 and the further non-volatile memory are implemented with a solid state drive (SSD), for example. Note that the non-volatile memories 124 and the further non-volatile memory are not limited to a SSD, they may be implemented with another form of non-volatile storage device. The above-mentioned volatile memory is a dual data rate (DDR)-form memory, for example. Note that the above-mentioned volatile memory is not limited to a DDR form, and it may be implemented with any other form volatile memory.

The aggregation section 15 stores, under control of the PCIe switches 125 or the FPGA 123, stores in the further non-volatile memory some of the imaging data having being stored in the volatile memory, the some of the imaging data corresponding to a center detection area in the detection surface, the center detection area including a center line that passes through the center of the detector surface and extends in the rotation direction. The center detection area is, for example, an area for detecting radiation used for a monitoring scan performed on the subject. The monitoring scan is performed to, for example, detect a contrast agent injected into the subject. Therefore, the center detection area is, for example, a range smaller than the detection surface, including the center line. In other words, the center detection area corresponds to, in the detection surface, an area of a center portion having a long axis extending in the channel direction and a short axis extending in the column direction.

As described above, with the CT imaging system according to the present application example, in for example a monitoring scan, or the like, imaging data in the center detection area can be transmitted to the process computer by accessing the further non-volatile memory, without accessing all of the non-volatile memories. With this configuration, the CT imaging system according to the present application example can improve the transfer efficiency of imaging data in a monitoring scan that uses the center detection area. With this configuration, the CT imaging system according to the present application example can improve the examination efficiency, i.e., the throughput for the examinations.

When the technical features of the present embodiment are achieved by a radiation imaging system, the radiation imaging system includes: the rotating portion 11; the non-rotating portion 12 including a process computer to process imaging data having being transmitted from the rotating portion 11; and the slip ring 105 configured to transmit the imaging data between the rotating portion 11 and the non-rotating portion 12. The rotating portion 11 includes a radiation source configured to generate radiation to be incident on an object; a detector device (detector section 13) configured to detect radiation having being transmitted through the object; a storage device (storage section 14) configured to store imaging data generated from the detector device; and an aggregator (aggregation section 15) configured to aggregate the imaging data stored in the storage device. The storage device includes the plurality of removable non-volatile memories 124 arranged in a manner corresponding to the plurality of detector elements in the detector device regarding an output from the detector device and an input to the aggregator. In this situation, the detector device 13 in the radiation imaging system may include the plurality of detector elements 101, and each of the detector elements 101 may be electrically connected with at least one corresponding non-volatile memory 124. The structural elements, processing, effects, etc., of the radiation imaging system are the same as those of the embodiments, and their explanation is not repeated.

When the technical features of the present embodiment are achieved by a method of acquiring computer-tomography (CT) imaging data, the method includes: generating CT imaging data of an object by the plurality of detector elements 101 at a rotating side of a CT imaging apparatus; providing at least one non-volatile memory 124 to each of the detector elements 101 at the rotating side; storing the CT imaging data from each of the detector elements 101 to the non-volatile memory 124 corresponding to the detector element 101; combining the CT imaging data stored in the non-volatile memory 124 of each of the detector elements 101 into aggregated CT imaging data at the rotating side; and transmitting the aggregated CT imaging data across a slip ring of the CT imaging apparatus to a stationary side of the CT imaging apparatus. The processing procedures, effects, etc., in the method of acquiring CT imaging data are the same as those of the embodiments, and their explanation is not repeated.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description.

With at least one of the embodiments as described above, it is possible to store imaging data collected through detection of radiation in a non-volatile memory such that the imaging data can be transmitted at a high data rate via a slip ring.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Regarding the embodiments and the like described above, the following notes are disclosed as certain aspects and selected characteristics of the present disclosure.

Note 1:
The FPGA may be configured to control the detector elements as PCIe (peripheral component interconnect express) devices.

Note 2:
The storage section may control the detector elements and the storage section as NVME (non-volatile memory express)-interface devices.

Note 3:
The storage section may be integrated within the aggregation section.

Note 4:
The CT imaging system may further include a slip ring connecting a rotating portion and a stationary portion of the CT imaging system.

Note 5:
The detector section, the storage section, and the aggregation section may be arranged in the rotating portion.

Note 6:
The CT imaging system may further include a pair of PCIe buses across the slip ring.

Note 7:
The CT imaging system may further include a process computer to process data transmitted from the aggregation section via the slip ring.

Note 8:
The process computer may further include a file system configured to directly access the detector section, the storage section, and the aggregation section.

Note 9:
The detector device may further include a plurality of detector elements, and each of the detector elements may be further electrically connected with at least one corresponding non-volatile memory.

What is claimed is:

1. A computer-tomography (CT) imaging system, comprising:
   an imaging data acquisition structure, comprising:
      a detector section comprising a plurality of detector elements configured to convert radiation into electric signals that carry imaging data;
      an aggregation section configured to aggregate the imaging data carried by the electric signals from the detector section; and
      a storage section arranged in a manner corresponding to the detector elements regarding an output from the detector section and an input to the aggregation section, wherein the storage section comprises a plurality of non-volatile memories configured to store the imaging data from the detector elements, and wherein each non-volatile memory of the plurality of non-volatile memories is configured to simultaneously store the imaging data of multiple images from a respective one or more of the plurality of detector elements.

2. The CT imaging system according to claim 1, wherein each of the detector elements includes a predetermined number of detector crystals converting X-ray photons into the electric signals.

3. The CT imaging system according to claim 2, wherein the non-volatile memories are arranged in association with the detector crystals.

4. The CT imaging system according to claim 1, further comprising a plurality of ASICs (application-specific integrated circuits) each being configured to sample the electric signals from one or more corresponding detector elements of the detector elements.

5. The CT imaging system according to claim 1, wherein the storage section includes a field programmable gate array (FPGA) connected to the detector elements and the FPGA is connected with a predetermined number of the non-volatile memories.

6. The CT imaging system according to claim 1, wherein the storage section is programmed in parallel by multicasting PCIe IO (input/output) commands to trigger the detector elements to collect simultaneously.

7. The CT imaging system according to claim 1, wherein the non-volatile memories are removable from the imaging data acquisition structure.

8. The CT imaging system according to claim 1, wherein the aggregation section comprises a plurality of PCIe switches arranged in a tree topology.

9. The CT imaging system according to claim 1, wherein the storage section is integrated within the detector section.

10. The CT imaging system according to claim 1, wherein the detector section, the storage section, and the aggregation section are in the form of three separate modules.

11. The CT imaging system according to claim 1, wherein the storage section is arranged between the detector section and the aggregation section and further arranged within the detector section.

12. The CT imaging system according to claim 1, wherein the storage section is arranged within the detector section and is further arranged within the aggregation section.

13. The CT imaging system according to claim 1, wherein the storage section is arranged between the detector section and the aggregation section and is further arranged within the aggregation section.

14. The CT imaging system according to claim 1, wherein
the plurality of detector elements are arranged in a rotation direction of a rotating portion of the CT imaging system, and
a capacity of some of the non-volatile memories electrically connected with some of the plurality of detector elements that are positioned at both ends in the rotation direction is smaller than a capacity of one of the non-volatile memories electrically connected with one of the plurality of detector elements positioned in a center portion in the rotation direction.

15. The CT imaging system according to claim 1, wherein
the plurality of detector elements are arranged in a rotation direction of a rotating portion of the CT imaging system, and
some of the plurality of detector elements that are positioned at both ends in the rotation direction are electrically non-connected with any of the non-volatile memories.

16. The CT imaging system according to claim 1, wherein
the imaging data acquisition structure further includes a plurality of detector sections and a plurality of storage sections, and
the CT imaging system further includes a file system that is configured to simultaneously access a predetermined number of the detector sections, a predetermined number of the storage sections, and the aggregation section.

17. The CT imaging system according to any one of claim 1, wherein the storage section further includes a volatile memory upstream of the non-volatile memories.

18. The CT imaging system according to claim 17, further comprising a rotating portion on which the detector section, the storage section, and the aggregation section are mounted, the rotating portion being rotatable around a rotation axis, wherein
the plurality of detector elements are arranged in a rotation direction of the rotating portion,
the aggregation section further includes an additional non-volatile memory different from the non-volatile memories, and
the aggregation section stores in the additional non-volatile memory some of the imaging data having being stored in the volatile memory, the some of the imaging data corresponding to a partial detection area of a detection surface, the detection surface being formed by the plurality of detector elements for detecting the radiation, the partial detection area including a center line that passes through a center of the detector surface and that extends in the rotation direction.

19. A radiation imaging system, comprising:
a rotating portion on which
a radiation source configured to generate radiation to be incident on an object;
a detector device comprising a plurality of detector elements configured to detect radiation having been transmitted through the object and generate imaging data based on the detected radiation;
a storage device configured to store the imaging data generated by the detector device; and
an aggregator configured to aggregate the imaging data stored in the storage device
are mounted;
a non-rotating portion, comprising a process computer to process the imaging data having being transmitted from the rotating portion; and
a slip ring configured to transmit the imaging data between the rotating portion and the non-rotating portion,
wherein the storage device includes a plurality of non-volatile memories arranged in a manner corresponding to the plurality of detector elements in the detector device regarding an output from the detector device and an input to the aggregator,
wherein during a scan the rotation portion rotates around the object and each detector element of the plurality of detector elements generates respective imaging data for multiple images, and
wherein each non-volatile memory of the plurality of non-volatile memories is configured to simultaneously store the respective imaging data for the multiple images that were generated by a respective one or more detector elements of the plurality of detector elements.

20. A method of acquiring computer-tomography (CT) imaging data, comprising:
while rotating a rotating side of a CT imaging apparatus around an object, generating CT imaging data for multiple images of the object by a plurality of detector elements in a detector section on the rotating side of the CT imaging apparatus;
providing, at the rotating side, a storage section and an aggregation section, wherein the storage section is arranged in a manner corresponding to the detector elements regarding an output from the detector section and an input to the aggregation section, and wherein the storage section comprises a plurality of non-volatile memories that are in communication with the detector elements at the rotating side;
simultaneously storing, in each non-volatile memory of the plurality of non-volatile memories, the CT imaging data for the multiple images from a respective one or more of the plurality of detector elements;
combining, at the aggregation section, the CT imaging data stored in the plurality of non-volatile memories into aggregated CT imaging data at the rotating side; and
transmitting the aggregated CT imaging data across a slip ring of the CT imaging apparatus to a stationary side of the CT imaging apparatus.

* * * * *